US008816133B2

(12) United States Patent
Hoong et al.

(10) Patent No.: US 8,816,133 B2
(45) Date of Patent: *Aug. 26, 2014

(54) PROCESS OF PRODUCING POLYGLYCEROL FROM CRUDE GLYCEROL

(75) Inventors: Seng Soi Hoong, Kajang (MY); Zailan Abu Bakar, Kajang (MY); Nik Siti Mariam Nek Mat Din, Kajang (MY); Zainab Idris, Kajang (MY); Shoot Kian Yeong, Kajang (MY); Hazimah Abu Hassan, Kajang (MY); Salmiah Ahmad, Kajang (MY)

(73) Assignee: Malaysian Palm Oil Board (MPOB), Selangor Darul Ehsan (MY)

( * ) Notice: Subject to any disclaimer, the term of this patent is extended or adjusted under 35 U.S.C. 154(b) by 485 days.

This patent is subject to a terminal disclaimer.

(21) Appl. No.: 12/821,294

(22) Filed: Jun. 23, 2010

(65) Prior Publication Data
US 2011/0190545 A1    Aug. 4, 2011

(30) Foreign Application Priority Data

Jun. 25, 2009   (MY) .............................. PI 20092692

(51) Int. Cl.
| C07C 41/01 | (2006.01) |
| C08G 65/48 | (2006.01) |
| C08G 65/34 | (2006.01) |
| C07C 41/09 | (2006.01) |

(52) U.S. Cl.
CPC ................ C08G 65/34 (2013.01); C08G 65/48 (2013.01); C07C 41/09 (2013.01)
USPC .......................................... 568/619; 568/621

(58) Field of Classification Search
None
See application file for complete search history.

(56) References Cited

U.S. PATENT DOCUMENTS 3,356,738 A * 12/1967 Hauser et al. ................. 568/621
3,932,532 A *  1/1976 Hunter et al. ................. 568/613

FOREIGN PATENT DOCUMENTS

| EP | 0 518 765 | 12/1992 |
| EP | 0 719 752 | 7/1996 |
| WO | 2004/065343 | 8/2004 |
| WO | 2007/049950 | 5/2007 |

OTHER PUBLICATIONS

Co-pending U.S. Appl. No. 12/776,092, filed May 7, 2010.*
European Search Report, dated Nov. 15, 2010 for European Application No. 10162361.9.
Soares et al., Soybean—Applications and Technology, Chapter 9—New Applications for Soybean Biodiesel Glycerol, pp. 151-172, 2011.
U.S. Appl. No. 12/776,092, file May 7, 2010, Office Action dated Sep. 25, 2012.
U.S. Appl. No. 12/776,092, filed May 7, 2010, Final Office Action dated Apr. 5, 2013.

* cited by examiner

Primary Examiner — Rosalynd Keys
(74) Attorney, Agent, or Firm — Workman Nydegger

(57) ABSTRACT

Accordingly, the present invention provides a process for preparing polyglycerol from crude glycerol, wherein the crude glycerol having a glycerol content from about 60 to about 90%, soap content from about 10 to about 15% and methanol content from about 5 to about 20%, the process includes the steps of (a) heating the crude glycerol that contains soap to an elevated temperature for a certain reaction time, (b) acidifying the crude polyglycerol with mineral acid at a specific temperature and (c) centrifuging the acidified crude product obtained from step (b) at specific temperature for a certain duration of time.

15 Claims, No Drawings

PROCESS OF PRODUCING POLYGLYCEROL FROM CRUDE GLYCEROL

FIELD OF INVENTION

The present invention relates to a process for producing polyglycerol from crude glycerol.

BACKGROUND OF INVENTION

Polyglycerols are commonly prepared through thermal dehydration of glycerol, in which the polymerisation was carried out at atmospheric pressure and at an elevated temperature, which is about 230° C.-270° C. The process can be accomplished without the use of catalyst but the yield of polyglycerol is considerably low.

Therefore, various catalysts have been introduced to aid in the formation of polyglycerol and the most commonly used catalysts are alkaline catalysts such as sodium or potassium hydroxide, alkaline carbonates such as potassium carbonate with aluminium oxide and alkaline earth metal hydroxide such as calcium hydroxide.

Acidic catalysts were also used in the thermal dehydration of glycerol such as mixtures of sulphuric acid and triacetin, hypophosphorus acid with sodium hydroxide and acidic zeolite. In addition, clay such as hydrotalcite was also used to catalyse thermal dehydration of glycerol.

Polyglycerol formation was also reported with either solketal, glycidol or glycerol carbonate as the reactants when reacted with hydrotalcite at elevated temperatures. In addition, glycidol, glycerol carbonate and solketal were polymerised using the fluoride salts of rubidium, caesium and potassium into polyglycerol. Both linear and cyclic polyglycerols were reported as products of reaction between glycidol, glycerol carbonate and solketal with β-zeolites as catalysts.

A process to produce polyglycerol, which comprised reacting glycerol, diglycerol or higher polyglycerol with epichlorohydrin at 90° C. to 170° C. to produce a crude chlorohydrin/ether mixture, followed by adding an amount of strong base at least substantially equivalent to the organically bound chlorine content of the chlorohydrin/ether mixture, and desalting the mixture and recovering the glycerol, diglycerol and higher polyglycerol fractions has also been disclosed in the prior art.

Allyl alcohol is another route in preparing polyglycerols. The process involved epoxidation of the allyl alcohol, in which glycidol would be formed and then followed by polymerisation of the glycidol. This was proven as another effective method to prepare polyglycerol.

Despite the fact that the background art in preparing polyglycerol is crowded and diverse, it is evident that the synthesis of polyglycerol and diglycerol from glycerol has several drawbacks. One of the drawbacks is the use of high purity compounds such as glycerol, epiclorohydrin, glycidol, glycerol carbonate and solketal as the starting material in the preparation of polyglycerol. These chemical compounds are expensive and their cost makes up the bulk of the production cost of polyglycerol.

Another drawback of the prior arts is the fact that most of the prior arts needed catalysts that were introduced to the reactants at certain point of the production process. The introduction of catalyst to the reactants also increases the production cost of polyglycerol.

Therefore, it is an objective of this invention to provide a process that uses feedstock of lower purity, which contains a suitable catalyst for the reaction. This invention would provide a process to produce polyglycerol with lower production cost.

SUMMARY OF THE INVENTION

Accordingly, the present invention provides process for preparing polyglycerol from crude glycerol, the process includes the steps of (a) heating the crude glycerol that contains soap to an elevated temperature for a certain reaction time, (b) acidifying the crude polyglycerol with mineral acid at a specific temperature and (c) centrifuging the acidified crude product obtained from step (b) at specific temperature for a certain duration of time.

The present invention consists of several novel features and a combination of parts hereinafter fully described and illustrated in the accompanying description, it is being understood that various changes in the details may be made without departing from the scope of the invention or sacrificing any of the advantages of the present invention.

DETAILED DESCRIPTION OF THE PREFERRED EMBODIMENTS

The present invention relates to a process for producing polyglycerol from crude glycerol. Hereinafter, this specification will describe the present invention according to the preferred embodiments of the present invention. However, it is to be understood that limiting the description to the preferred embodiments of the invention is merely to facilitate discussion of the present invention and it is envisioned that those skilled in the art may devise various modifications and equivalents without departing from the scope of the appended claims.

The present invention provides improvement to the current method of producing polyglycerols from glycerol. The improvement in this invention was made evident by the use of lower quality (cheaper) feedstock that contained suitable catalyst for the process. Preferably, the lower quality feedstock is crude glycerol derived from biodiesel plant. More specifically, the crude glycerol is the by-product from the production of methyl ester (biodiesel).

For this invention, it was preferred that the biodiesel derived crude glycerol's composition consisted of 60 to 90% glycerol, 10 to 25% methanol and 10 to 15% soap. More preferably, the crude glycerol contained 80 to 90% glycerol, 1 to 10% methanol and at least 10% soap. High content of methanol in the crude glycerol will increase the reaction time needed to fully convert the crude glycerol to polyglycerol and this will incur higher production cost.

It has been reported that polymerisation of glycerol to form polyglycerol can be carried out without the use of catalyst but the reaction suffered low yield of polyglycerol. Therefore, in this invention, a catalyst was used to increase the yield and selectivity of products. We discovered that fatty acid salts of alkaline metal (soap) gave good yield and selectivity in producing polyglycerol (especially those with degrees of polymerization, "n," ranging from 2 to 6) from glycerol. The soap may be, for example, a sodium or potassium salt of fatty acids comprising 8 to 22 carbon atoms in chain length (C8 to C22). We have disclosed earlier that the preferred crude glycerol contained 10 to 15% soap and this soap acts as a catalyst for the thermal dehydration reaction of glycerol to polyglycerol.

The soap in the crude glycerol was formed during the transesterification reaction between triglycerides and methanol that yield methyl ester (biodiesel), where the free fatty acid in the biodiesel feedstock reacted with the transesterification catalyst (sodium or potassium hydroxide or sodium methoxide) to yield the soap. In the biodiesel production process, the soap was removed together with the crude glycerol as by-product.

Examples of soap but not limited to this that could be found in the crude glycerol are sodium or potassium laurate, myristate, palmitate, stearate, oleate and linoleate. Preferably, the soap in the crude glycerol is sodium palmitate or sodium oleate. The preferred amount of soap in the crude glycerol is 0.1% to 15% and more preferably the amount of soap in the crude glycerol is not less than 10%. Most preferably, the amount soap in the crude glycerol is 10 to 15%. If the crude glycerol contains less than 10% soap, then the conversion of crude glycerol to polyglycerol will not achieve 100%.

The thermal dehydration reaction of crude glycerol to polyglycerol could be carried out with any conventional heating method that is coupled with sufficient stirring capacity to ensure homogenous reaction. For this invention, it was preferred that the temperature be in the range of 200° C. to 290° C., but more preferably in the range of 250° C. to 270° C. By employing temperatures in this range, it is possible to achieve good conversion with minimal side product while still obtaining acceptable reaction rates. The most preferred reaction temperature was 270° C. as the conversion of crude glycerol to polyglycerol was 90%. The reaction time in one embodiment was 2 to 6 hours. The preferred reaction time was 3 to 5 hours in which the optimum conversion of crude glycerol to polyglycerol could be achieved in this time frame. It is particularly preferred aspect of the invention, that the process be conducted at atmospheric pressure and by such operation the use of costly high-pressure equipment is avoided.

Crude polyglycerols prepared from crude glycerol still contained soap that will cause the product to become solid. The soap in the product could be removed through acidification at 50-90° C. of the crude product with phosphoric acid or any other mineral acids such as sulphuric, hydrochloric and nitric acid. The amount of the mineral acid used for acidifying the crude product was in the range of 1 to 3% (w/w). The final pH of the acidified product was in the range of 4 to 6, preferably in the range of 4 to 5.

The acidified crude product was then subjected to centrifugation. The acidified crude product was heated to 40-90° C., preferably to 60-80° C. before the centrifugation process was started. The acidified crude product was centrifuged for at least 30 minute at 1500 to 2000 rpm. The centrifugal force was able to separate the fatty acid and salt from the product. The acidified crude product was separated into three layers after the centrifuge process. The top layer, was the fatty acid layer while the middle layer, was the purified polyglycerol. The bottom layer consists of salt and absorbed product.

The crude and purified polyglycerol samples were analyzed with High Performance Liquid Chromatography (HPLC) and the compositions of glycerol oligomers in each polyglycerol samples were determined. The HPLC system is equipped with an Evaporative Light Scattering Detector (ELSD). The samples analysis was achieved with a 25 cm×4.6 mm ID column prepacked with 10 μm Hypersil $NH_2$ amino at 30° C. An elution with acetonitrile (85%) and water (15%) was carried out at a flow rate of 1 ml/minute. The chromatographs were analyzed using software installed in the instrument to yield peak area and retention time. The samples were dissolved in water (2% w/v) and 20 μl of solution was injected by automatic loop injector.

Based on HPLC analysis results, the conversion of crude glycerol to polyglycerol reached 90% when the crude glycerol that contained 12% soap was subjected to thermal dehydration reaction at 270° C. for 3 hours. The following is the typical composition of glycerol oligomers in the purified polyglycerol as analysed by HPLC: —

Composition of Glycerol Oligomers
0%-10% of unreacted glycerol
20%-30% of diglycerol
30%-40% of triglycerol
20%-30% of higher polyglycerol According to the HPLC chromatogram, there is little or no evidence of cyclic diglycerol or polyglycerol found in the crude polyglycerol as it was compared to standard oligomers of glycerol. Therefore, the process can be claimed to be selective for producing linear diglycerol and polyglycerol from glycerol.

For comparison purpose, 10% sodium oleate (soap) was added into pure glycerol and the mixture was subjected to conventional heating at 270° C. for 6 hours. HPLC analysis showed that 90% of pure glycerol could be converted to polyglycerol after 3 hours of reaction by conventional heating. Therefore, this has proven that 10% soap was sufficient to convert 90% of glycerol to polyglycerol and 3 hours of thermal dehydration reaction at 270° C. was sufficient for good conversion of glycerol to ploglycerol.

The following examples demonstrate the invention and facilitate its understanding:

Example 1

Biodiesel derived crude glycerol (100 g) that contained 80% glycerol, 12% soap and 6% methanol was charged into a three-necked 250 ml round bottom flask. The round bottom flask was connected to a condenser to collect any distillate. The content of the round bottom flask was heated to 270° C. for 3 hours by using conventional heating. The crude product was analysed by HPLC and the following are the composition of the crude product. The conversion percentage of crude glycerol to polyglycerol was about 90% after 3 hours of reaction.

Composition of Glycerol Oligomers in Crude Polyglycerol
10% of glycerol
30% of diglycerol
40% of triglycerol
20% of higher polyglycerol

Example 2

The experiment in Example 1 was repeated with pure glycerol that contained 10% sodium oleate as the catalyst. The content of the round bottom flask was heated to 270° C. for 3 hours by using conventional heating. The crude product was analysed by HPLC and the following are the composition of the crude product. The conversion percentage of pure glycerol to polyglycerol was about 90% after 3 hours of reaction.

Composition of Glycerol Oligomers in Crude Polyglycerol
10% of glycerol
32% of diglycerol
28% of triglycerol
30% of higher polyglycerol

Example 3

The crude polyglycerol from Example 1 was subjected to a process to remove the soap in the crude product. The crude product was heated to 90° C. while stirring it with a magnetic stirrer and the acidification of the crude product was monitored by pH value. The initial pH of the crude product was about 9 and phosphoric acid was added drop-wise to the crude glycerol until the pH of the crude glycerol reached about 4.

The acidified crude product was stirred for another 30 minute before transferring the acidified product to a centrifuge instrument. Under acidic condition, the soap was hydrolyzed to yield fatty acid and the sodium ion ($Na^+$) formed salt (sodium phosphate) with phosphoric acid. The centrifuge instrument was set to 60° C. and the acidified crude product was centrifuged for 30 minute at 1600 rpm. The acidified product was separated into 3 layers, in which the middle layer was the purified polyglycerol. The purified polyglycerol was then subjected to HPLC analysis and the compositions of each oligomers of glycerol are shown as below.

Composition of Glycerol Oligomers in Purified Polyglycerol
- 10% of glycerol
- 30% of diglycerol
- 40% of triglycerol
- 20% of higher polyglycerol

The invention claimed is:

1. A process for selectively preparing linear polyglycerol, with no cyclic polyglycerol formation, the linear polyglycerol being prepared from crude glycerol, wherein the crude glycerol has a glycerol content from about 60 to about 90% and soap content from about 10 to about 15% and methanol content from about 1 to about 25%, the process includes the steps of:
   a. heating the crude glycerol that contains soap for a reaction time such that about 90% or more of the glycerol is converted to linear polyglycerol(s) with no cyclic polyglycerol formation;
   b. acidifying the crude polyglycerol with mineral acid; and
   c. centrifuging the acidified crude product obtained from step (b), the centrifuging without further separation techniques separating the acidified crude product into three layers including a fatty acid layer, a purified polyglycerol layer, and a salt layer.

2. A process according to claim 1 where the crude glycerol is a by-product from the transesterification process of triglycerides with alcohol.

3. A process according to claim 1 where the soap is sodium or potassium salt of fatty acids comprising 8 to 22 carbon atoms in a chain length (C8 to C22).

4. A process according to claim 1 where the reaction is conducted at a temperature from 230 to 290° C.

5. A process according to claim 1 where the reaction is conducted at atmospheric pressure.

6. A process according to claim 1 where the reaction is conducted for 2 to 6 hours.

7. A process according to claim 1 where the crude polyglycerol is acidified by a mineral acid selected from the group consisting of phosphoric acid, hydrochloric acid, sulphuric acid and nitric acid.

8. A process according to claim 1 where the crude polyglycerol is acidified by mineral acid to pH 4-6.

9. A process according to claim 1 where the crude polyglycerol is acidified at 50-90° C.

10. A process according to claim 1 where the acidified crude polyglycerol is centrifuged at 40-90° C.

11. A process according to claim 1 where the acidified crude polyglycerol is centrifuged for at least 30 minutes.

12. A process according to claim 1 where the acidified crude polyglycerol is centrifuged at 1500 to 2000 rpm.

13. A process according to claim 1 where the degree of polymerisation of crude polyglycerol varies from n=2 to 6.

14. A process for selectively preparing linear polyglycerol, with no cyclic polyglycerol formation, the linear polyglycerol being prepared from crude glycerol, wherein the crude glycerol has a glycerol content from about 60 to about 90% and soap content from about 10 to about 15% and methanol content from about 1 to about 25%, the process includes the steps of:
   a. heating the crude glycerol that contains soap to an elevated temperature within a range of 230 to 290° C. for a reaction time such that 90% or more of the glycerol is converted to linear polyglycerol(s) with no cyclic polyglycerol formation;
   b. acidifying crude polyglycerol resulting from step (a) with mineral acid; and
   c. centrifuging the acidified crude polyglycerol that has been processed in accordance with step (b) at a temperature from 40 to 90° C. for at least 30 minutes such that purified polyglycerol is separated from fatty acid and salt without requiring further separation techniques.

15. A process for selectively preparing linear polyglycerol, with no cyclic polyglycerol formation, the linear polyglycerol being prepared from crude glycerol, wherein the crude glycerol is a byproduct from production of methyl ester (biodiesel), the crude glycerol having a glycerol content from about 60 to about 90%, soap content from about 10 to about 15%, and methanol content from about 1 to about 25%, the process includes the steps of:
   a. heating the crude glycerol to an elevated temperature within a range of 230 to 290° C. for a reaction time such that 90% or more of the glycerol is converted to linear polyglycerol(s) with no cyclic polyglycerol formation;
   b. acidifying crude polyglycerol resulting from step (a) with mineral acid; and
   c. centrifuging the acidified crude polyglycerol product obtained from step (b) at a temperature from 40 to 90° C. for at least 30 minutes, the centrifuging without further separation techniques separating the acidified crude product into three layers including a fatty acid layer, as purified polyglycerol layer, and a salt layer.

* * * * *

UNITED STATES PATENT AND TRADEMARK OFFICE
CERTIFICATE OF CORRECTION

PATENT NO. : 8,816,133 B2  Page 1 of 1
APPLICATION NO. : 12/821294
DATED : August 26, 2014
INVENTOR(S) : Hoong et al.

It is certified that error appears in the above-identified patent and that said Letters Patent is hereby corrected as shown below:

In the Specification

Column 3
Line 12, change "the amount soap" to --the amount of soap--

Column 4
Line 22, change "ploglycerol" to --polyglycerol--

Signed and Sealed this
Seventh Day of July, 2015

Michelle K. Lee
*Director of the United States Patent and Trademark Office*